United States Patent [19]

Sarumaru et al.

[11] Patent Number: 4,551,571
[45] Date of Patent: Nov. 5, 1985

[54] PRODUCTION OF ALKENYLBENZENES

[75] Inventors: Kohei Sarumaru; Tomoatsu Iwakura, both of Ami; Yasuo Yoshino; Toshimichi Ito, both of Hasaki; Akikazu Watanabe; Mikio Mori, both of Mie, all of Japan

[73] Assignee: Mitsubishi Petrochemical Co., Ltd., Tokyo, Japan

[21] Appl. No.: 708,743

[22] Filed: Mar. 6, 1985

[30] Foreign Application Priority Data

Mar. 14, 1984 [JP] Japan ................................ 59-48453
Mar. 14, 1984 [JP] Japan ................................ 59-48454

[51] Int. Cl.$^4$ ............................ C07C 4/02; C07C 2/64
[52] U.S. Cl. ................................... 585/440; 585/444; 585/445
[58] Field of Search ...................... 585/440, 444, 445

[56] References Cited

U.S. PATENT DOCUMENTS 3,223,743 12/1965 MacFarlane ........................ 585/444

Primary Examiner—Curtis R. Davis
Attorney, Agent, or Firm—Robert E. Burns; Emmanuel J. Lobato; Bruce L. Adams

[57] ABSTRACT

A method for producing an alkenylbenzene by catalytically dehydrogenating an alkylbenzene non-oxidatively in the presence of steam in the reaction zone comprising a fixed-bed of potassium-containing dehydrogenation catalyst particles, wherein the potassium-containing dehydrogenation catalyst particles are prevented from powdering by (a) using a fixed-bed comprising particles of at least two kinds of potassium-containing dehydrogenation catalyst with respectively different potassium contents and (b) arranging the catalyst particles so that those with higher potassium content are not disposed on the inlet side of said catalyst bed with respect to the reaction.

6 Claims, 2 Drawing Figures

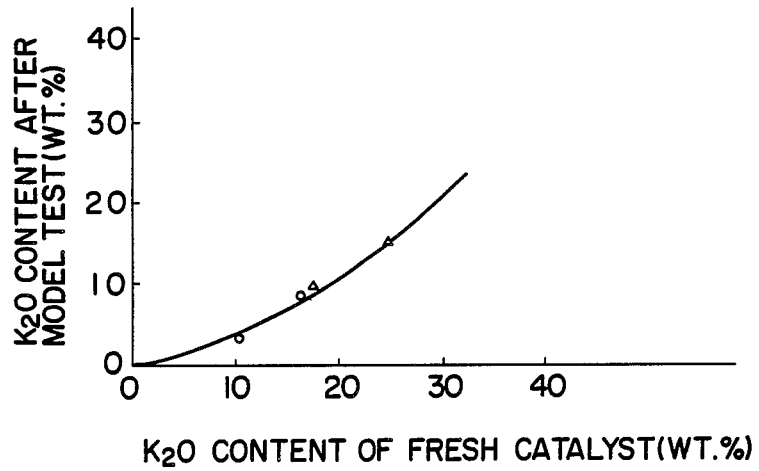

PRODUCTION OF ALKENYLBENZENES

BACKGROUND OF THE INVENTION

1. Field of the Invention

This invention relates to production of alkenylbenzenes by catalytic dehydrogenation of alkylbenzenes over a potassium-based dehydrogenation catalyst. More particularly, the present invention pertains to a method for production of alkenylbenzenes which is featured primarily in the manner in which the fixed-bed of the potassium-based dehydrogenation catalyst is arranged.

The present invention, in another aspect thereof, also concerns prevention of catalyst degradation or powdering which has been difficult to avoid in a potassium-based dehydrogenation catalyst to be used for catalytic dehydrogenation of alkylbenzenes.

2. Prior art

Dehydrogenation reaction of an alkylbenzene, such as from ethylbenzene to styrene, or from p-methylethylbenzene to p-methylstyrene, etc., is industrially a very important reaction.

These reactions are carried out generally by bringing a starting alkylbenzene together with heated steam into contact with a dehydrogenation catalyst in an adiabatic system or an isothermal system reactor.

As the dehydrogenation catalyst to be used in the above reaction, potassium-based catalysts have been widely known for their excellent activity and selectivity.

As such potassium-based catalysts, $K_2O\text{-}Fe_2O_3\text{-}Cr_2O_3$ catalysts and $K_2O\text{-}Fe_2O_3\text{-}CeO_2$ catalysts containing $K_2O\text{-}Fe_2O_3$ as the main component are industrially useful, and many catalysts of these systems have been proposed and are commercially available.

However, most of these catalysts, while having respective excellent features on one hand, involve problems on the other. Thus, it can be said that no catalyst which satisfies requirements as an industrial catalyst with respect to high activity, high selectivity, long life, and low cost, has yet been known.

In particular, when an alkenylbenzene is to be produced by carrying out the above reaction by the use of an industrially more practical adiabatic system reactor, it is required for reduction of its production cost to employ reaction conditions in which the amount of steam employed, that is, the steam/starting alkylbenzene (molar ratio), is lowered. In this case, if an alkenylbenzene is intended to be produced in a high yield with the use of a highly selective catalyst of the above known catalysts, the life of the catalyst becomes very short, and such a catalyst has proved to be unsatisfactory as a catalyst for industrial production in the present state of the art. In this respect, the analysis we have conducted is described in detail hereinafter.

Concerning the arrangement of the catalyst during production by catalytic dehydrogenation of an alkylbenzene, there is a disclosure in the specification of U.S. Pat. No. 3,223,743. However, it does not appear to us that the invention disclosed in this patent refers to the problem of the catalyst life.

BRIEF DESCRIPTION OF THE DRAWING

In the drawing:

FIG. 1 is a graph showing the relationship between the $K_2O$ content in the fresh catalyst used for the model test of dehydrogenation reaction of ethylbenzene and the $K_2O$ content after the model test; and FIG. 2 is a graph showing the relationship between the $K_2O$ content in the fresh catalyst and the percentage of catalyst degradation after the model test.

In FIGS. 1 and 2, the mark Δ indicates a $Fe_2O_3\text{-}K_2O\text{-}CeO_2$ catalyst, and the mark o indicates a $Fe_2O_3\text{-}K_2O\text{-}Cr_2O_3$ catalyst.

SUMMARY OF THE INVENTION

The present invention provides a method for practicing production of an alkenylbenzene by catalytic dehydrogenation of an alkylbenzene in a high yield and while maintaining a long catalyst life.

The present invention, in one aspect thereof, provides a method for producing an alkenylbenzene by catalytically dehydrogenating an alkylbenzene under non-oxidative conditions in the presence of steam in the reaction zone comprising a fixed-bed of potassium-containing dehydrogenation catalyst particles, wherein an improvement is provided in that (a) the fixed-bed comprises at least two kinds of potassium-containing dehydrogenation catalyst particles with respectively different potassium contents and in that (b) the catalyst particles with higher potassium content are not disposed on the upstream side, with respect to the reaction, of the fixed-bed.

According to one mode of practice of the invention wherein the catalyst particles with greater potassium content are not arranged on the upstream side of the fixed-bed, the catalyst particles with greater potassium content are arranged on the downstream side of the fixed-bed with respect to the reaction, thus increasing the potassium content in the catalyst bed from the upstream side toward the downstream side. According to another mode of the invention, the catalyst particles with higher potassium content and the catalyst particles with lower potassium content are mixed substantially homogeneously, thereby making the potassium content in the catalyst bed substantially the same from the upstream side to the downstream side.

The present invention, in another aspect thereof, provides a method for preventing a potassium-based dehydrogenation catalyst for catalytical dehydrogenation of alkylbenzene under non-oxidative conditions in the presence of steam from being degraded during the dehydration process, which method comprises (a) using a fixed-bed comprising at least two kinds of potassium-based dehydrogenation catalyst particles of respectively different potassium contents, (b) the catalyst particles with higher potassium content not being arranged on the upstream side of the catalyst bed.

The modes of practice of this invention in this aspect are the same as the two modes in the first aspect as described above in connection with the manner of arrangement of the catalyst particles with different potassium contents.

DETAILED DESCRIPTION OF THE INVENTION

Analysis of the reaction

We have made a detailed analysis of catalyst behaviors in the case of production of alkenylbenzenes by non-oxidative catalytic dehydrogenation reaction of alkylbenzenes at an elevated temperature in the presence of a potassium-based catalyst by use of an adiabatic fixed-bed reactor in order to make possible production of alkenylbenzenes in high yield without reducing the catalyst life even under the conditions where the amount of steam employed is reduced.

We first investigated the reaction characteristics and the catalyst compositions of various kinds of commercially available catalysts of the $Fe_2O_3$-$K_2O$-$Cr_2O_3$ system and the $Fe_2O_3$-$K_2O$-$CeO_2$ system containing $Fe_2O_3$-$K_2O$ as the main component. As a result, it was found that these catalysts contained a diversity of additive components in addition to the above main catalyst component and are affected also by these additive components, but the reaction characteristics of the catalyst were greatly predominated by the content of $K_2O$ contained therein. That is, the catalyst with higher $K_2O$ content is highly selective but has a relatively lower activity, while the catalyst with lower $K_2O$ content is highly active but has relatively lower selectivity.

Next, we investigated the relationship between the $K_2O$ content and the catalyst life according to a model test by the use of various kinds of commercially available catalysts (all extruded products with diameter of about $\frac{1}{8}$ inch) as follows.

Each catalyst (50 ml) was packed in a $\frac{1}{2}$-inch U-tube reactor made of SUS 304 (J.I.S.) placed in a fluid bath heater. Under the conditions of a reaction bath temperature of 600° C., a pressure of 1 Kg/cm$^2$-G, a feed molar ratio of steam/starting ethylbenzene of 6 and LHSV of 1 Hr$^{-1}$, the reaction for production of styrene was carried out continuously for about 600 hours.

After the reaction, the total amount of the catalyst was taken out, and the powdered catalyst was screened through a metal 10-mesh sieve and weighed. For the portion not powdered, the $K_2O$ content in the catalyst was measured by "Model 3064 Fluorescent X-ray Analyzer" produced by Rigaku Denki K.K., Japan.

The results of the model tests are shown in FIG. 1 [$K_2O$ content (wt.%) in fresh catalyst -$K_2O$ content (wt.%) after model test], and FIG. 2 [$K_2O$ content (wt.%) in fresh catalyst -powdering of catalyst after model test (wt.%)].

FIG. 1 suggests that the behaviors concerning loss of potassium are approximate to each other in both of the potassium-containing catalysts of $Fe_2O_3$-$K_2O$-$Cr_2O_3$ system and $Fe_2O_3$-$K_2O$-$CeO_2$ system, and FIG. 2 shows that powdering of the catalyst occurs in the amount corresponding to the $K_2O$ content in the catalyst.

The results of the above model tests provide very important and new findings. More specifically, while various presumptions have been formerly made about the causes for deterioration of these catalyst systems without any clue leading to the core of the problem, the powdering phenomenon of the catalyst accompanying the loss of potassium, which is a new discovery made by us as described above, may be considered to be one of factors of crucial importance for the deterioration of the catalyst.

This new finding will be a very important factor, particularly when the production cost of alkenylbenzene is to be lowered by reduction of the steam feed rate in an adiabatic fixed-bed reactor. More specifically, reduction of the steam feed rate in an adiabatic reactor will, since this dehydrogenation reaction is a highly endothermic reaction and the steam has a large heat capacity, require to elevate the inlet temperature of the reactor, as can be readily calculated from the heat balance calculation.

On the other hand, it is reasonable to consider that loss (possibly through sublimation) of potassium occurs as the result of reduction (hydrogenation) of $K_2O$, and it can easily be thought of from common knowledge in inorganic chemistry that the temperature dependence of the reduction of $K_2O$ with hydrogen is very great. This was also confirmed by a thermodynamic calculation of temperature dependence of the equilibrium partial pressure of potassium according to the reaction scheme:

$$K_2CO_3 + H_2 \rightarrow K + CO_2 + H_2O \quad [I]$$

or

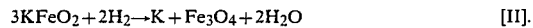

$$3KFeO_2 + 2H_2 \rightarrow K + Fe_3O_4 + 2H_2O \quad [II].$$

Also, the steam partial pressure is a great factor affecting loss of potassium as will be apparent from the above scheme [I] or [II], a reduction in the steam feed resulting in an increase of loss of the potassium. Thus, employment of low steam feed rate leads to increase of potassium scattering from both aspects of temperature and equilibrium partial pressure.

Next, the relationship between loss of potassium and powdering of the catalyst was examined. The strength of the commercially available potassium-containing catalyst produced by extrusion molding does not depend very much on the function as a binder of $K_2O$ when the content of $K_2O$ is low, but it may be considered that the catalyst strength is largely dependent on the function as a binder of $K_2O$ when its content is greater.

To summarize simply the relationship of the knowledge obtained from the model tests as described above, $K_2O$ content, and the reaction characteristic: under the condition of low steam/starting alkylbenzene ratio (molar ratio), when (a) high yield and (b) long life are considered as the required performance items demanded for the catalyst employed, it can be derived that the preferable directions of the respective performances (a) and (b) demanded for the catalyst are opposite with respect to the content of $K_2O$.

That is, a catalyst with longer life must have a lower $K_2O$ content and be of a high activity type, while a catalyst with higher yield must have a higher $K_2O$ content and be of a high selectivity type. These conclusions are fundamentally antagonistic to each other, and it was concluded that it is fundamentally difficult to obtain high yield and long life at the same time with a single catalyst under the condition of low steam/starting alkylbenzene ratio (molar ratio).

Particularly, degradation of catalyst particles through loss of potassium may sometimes cause a serious disorder in a reactor. For example, there may be mentioned loss of the catalyst bed at the inlet portion of the reactor, and also concretion at the inner portion of the catalyst bed caused by inflow of the degraded or powdered catalyst particles into the catalyst bed and depositing of the "sublimed" potassium.

The concretion phenomenon within the catalyst bed will prevent uniform flow of gas stream through the catalyst bed, thereby further shortening the catalyst life.

Such a concretion phenomenon may be considered to be one of the characteristics of an adiabatic fixed-bed reactor. That is to say, in the non-oxidative dehydrogenation reaction with the use of an adiabatic fixed-bed reactor, due to its characteristic of greatly endothermic reaction, the temperature within the catalyst bed abruptly drops with the progress of the dehydrogenation reaction although the temperature at an inlet or upstream portion of the catalyst bed may be high, whereby the temperature becomes lower toward the outlet or downstream portion of the catalyst bed. Accordingly, the potassium 'sublimed' from the inlet portion of the catalyst bed may be considered to deposit within and the downstream portion of the catalyst bed.

First Mode of Practice of the Invention

However, we have found a method for overcoming the problems in the conclusion as described above.

That is, we noticed that the temperature distribution characteristics possessed by the adiabatic fixed-bed reactor solve the above problems. Generally speaking, since the non-oxidative dehydrogenation reaction by the use of an adiabatic fixed-bed reactor is a greatly endothermic reaction, the gas inlet or upstream portion of the catalyst bed is at a high temperature, but the inner temperature within the catalyst bed will abruptly drop with the progress of the dehydrogenation reaction. The temperature drop will be greater when the feed rate of the steam is lowered. Accordingly, the above mentioned method is to arrange catalyst particles with different potassium contents according to the temperature distribution within the reaction bed.

More specifically, according to this first mode of the invention, there is provided a method for producing an alkenylbenzene by catalytically dehydrogenating an alkylbenzene under a non-oxidative condition in the presence of a potassium-based dehydrogenation catalyst and steam by the use of an adiabatic fixed-bed reactor, wherein at least two kinds of potassium-based dehydrogenation catalysts with respectively different potassium contents are so arranged that the catalyst with lower potassium content is on the upstream side of the catalyst bed and the catalyst with greater potassium content is on the downstream side of the catalyst bed.

According to the method of the present invention, due to substantially no loss (possibly through sublimation) of potassium within the dehydrogenation reactor, powdering can be suppressed to a minimum to obtain an elongation of the catalyst life. Further, according to the method of the present invention, it becomes possible to obtain an alkenylbenzene in a high yield and yet with high selectivity. The reason for this may be considered to be as follows. At the portion of the reactor near its inlet, where the catalyst with lower potassium content ($K_2O$ content) is disposed, although the catalyst employed may have a relatively high ability to decompose the alkenylbenzene formed, lowering of the selectivity is small on account of a lower alkenylbenzene concentration, while at the downstream portion in the reactor with higher $K_2O$ content, the catalyst has a lower ability to decompose the alkenylbenzene formed and therefore can exhibit high selectivity in spite of a higher concentration of alkenylbenzene.

As a known technique having its specific feature in the arrangement of the catalyst in the dehydrogenation of alkenylbenzene, reference is made to U.S. Pat. No. 3,223,743, which discloses a method for producing an alkenylbenzene in a high yield when the catalyst bed in the reactor is divided into a bed with higher selectivity arranged at the inlet portion and a bed with higher activity arranged at the outlet portion. Thus, this known technique recommends an arrangement of the catalysts which is just contrary to that of the method of the present invention.

The potassium-based dehydrogenating catalyst to be used in the method of the present invention is inclusive of those comprising $K_2O$-$Fe_2O_3$ as the main component such as $K_2O$-$Fe_2O_3$-$Cr_2O_3$ catalyst and $K_2O$-$Fe_2O_3$-$CeO_2$ catalyst. Such catalysts are disclosed in, for example, Japanese Patent Publications Nos. 18361/1968 and 19864/1968, Japanese Laid-Open Patent Publication Nos. 65998/1974, 120887/1974, 12088/1974, 7889/1977, 53803/1977, 94295/1978, 129190/1978, 129191/1978 and 90102/1979.

Typical examples of such catalysts commercially available are "S-105", "S-015" and "S-005" produced by Shell Corp., U.S.A., and "G-64C", "G-64E", "G-64I" and "G-64F" produced by Girdler Corp., U.S.A., etc.

The method of the present invention is applicable also regardless of the molar ratio of steam/starting alkylbenzene, but, when applied for production of e.g. styrene from ethylbenzene, if it is applied with a molar ratio of steam/ethylbenzene of 12 or lower, preferably 10 or lower, the effectiveness of the present invention is marked, and styrene can be produced in a high yield maintained for a long term.

In this mode of the present invention, two or more kinds of potassium-based catalysts with different potassium contents are arranged in the reactor with the catalyst having the lower potassium content disposed on the upstream side of the starting material gas.

It is possible to employ various methods for arranging two or more kinds of potassium-based catalysts with different potassium contents so that the catalyst with lower potassium content is on the upstream side of the catalyst bed and that with higher potassium content is on the downstream side of the catalyst bed. For example, in one method the catalysts are arranged in successive beds; in another method the potassium concentration is increased from near the inlet toward the outlet direction by changing the mixing ratio of particles of at least two potassium-based catalyst species with different potassium contents.

Specifically, it is convenient to pack the particles of the catalysts in two successive beds and, in a radial flow type reactor, when the flow of the gas stream is from the inside toward the outside, the dehydrogenation catalyst with lower potassium content is packed in the bed on the inner side, while the dehydrogenation catalyst with higher potassium content is thus packed on the outer side. On the other hand, in a tank type down flow type reactor, the dehydrogenation catalyst with lower potassium content is packed in the upper bed at the inlet portion, and the dehydrogenation catalyst with higher potassium content is packed in the lower bed. Of course, it is possible to pack the catalysts respectively with a structure of two or more beds.

In this case, when there is a difference in potassium concentration of preferably 5 wt.% or more as $K_2O$ between the catalysts with different potassium contents to be used at the inlet portion and the outlet portion of the reactor, respectively, more preferable results can be obtained with respect to the alkenylbenzene yield and the catalyst life. It is a conventional technique to mix optionally the whole or a part of the catalyst bed with an inert diluent material such as Raschig rings or balls made of porcelain, and such a dilution of the catalyst bed may also be practiced in the present invention.

Second Mode of Practice of the Invention

The second mode of the present invention concerns another approach for overcoming the conclusion and the problems indicated in the above analysis of the reaction.

More specifically, it is a method in which a mixture of particles of two or more kinds of a catalyst with lower $K_2O$ content and a catalyst with higher $K_2O$ content is employed as the potassium-based dehydrogenation catalyst to be used in the reactor. By this method, it has been clarified that the amount of the potassium "sublimed" from the inlet portion of the catalyst bed can be suppressed, and also concretion of the inner portion of the catalyst can be inhibited.

It must be said that the solution of the above problems by the method as described above was unexpected. Yet its reason may be attributed to the fact that, among the individual catalyst particles within the catalyst bed, those with lower $K_2O$ content consequently become lower in temperature on the surface or in the interior of the particles than those with higher $K_2O$ content, whereby potassium "sublimed" in gas phase deposits on the adjacent particles with lower $K_2O$ content to give rise to uniformization of $K_2O$ contained in the catalyst as a whole, thus inhibiting concretion.

Thus, according to this mode of the present invention, there is provided a method for producing an alkenylbenzene by non-oxidative catalytic dehydrogenation of an alkylbenzene at a high temperature under the presence of a potassium-based dehydrogenation catalyst in an adiabatic fixed-bed reactor, wherein particles of at least two kinds of dehydrogenation catalysts with respectively different potassium contents are arranged in a mixture in the reactor.

In this connection, as a known technique characterized by the arrangement of the catalyst in dehydrogenation of alkenylbenzene, reference is made to the Specification of U.S. Pat. No. 3,223,743, which discloses a method for producing an alkenylbenzene in high yield wherein the catalyst bed in the reactor is divided into a bed with higher selectivity disposed at the inlet portion and a bed with higher activity disposed at the outlet portion. Thus, the above known technique recommends an arrangement of the catalysts which is entirely different from that of the method of the present invention.

For the potassium-based dehydrogenation catalyst to be used in the second mode of the present invention, those as enumerated in the description of the first mode are also applicable.

This mode of the present invention may be applied also regardless of the molar ratio of steam/starting alkylbenzene, but when applied to the production of e.g. styrene from ethylbenzene, if it is applied at a molar ratio of steam/ethylbenzene of 12 or lower, preferably 10 or lower, the effectiveness of the present invention can be marked, and styrene can be produced while maintaining a high yield for a long period.

In this second mode of the present invention, particles of two or more kinds of potassium-based catalysts with different potassium contents may be mixed together and used.

In this case, when there is a difference in potassium concentration of preferably 5 wt.% or more, more preferably 8 wt.% or more, as $K_2O$ between the catalysts with different potassium contents, more preferable results can be obtained with respect to the alkenylbenzene yield and the catalyst life. It is of course possible to dilute the catalyst according to this embodiment appropriately with an inert diluting material.

Catalytic Dehydrogenation of Alkylbenzene

Except for the fixed-bed of potassium-based catalyst particles of the nature as described above, the non-oxidative catalytic dehydrogenation of an alkylbenzene in the present invention can be practiced under known reaction conditions. For example, in the case of production of styrene by dehydrogenation of ethylbenzene, it can be practiced at a temperature in the range of 570° to 660° C., a pressure in the range of 0.2 to 2.5 Kg/cm$^2$A, and a LHSV in the range of 0.1 to 1.5 Hr$^{-1}$.

To carry out the dehydrogenation reaction "adiabatically" means that substantially no heating from outside of the reactor is carried out, the heat necessary for the endothermic reaction being supplied by steam into the catalyst bed.

The present invention will now be described in greater detail with respect to the following Examples and Comparative Examples.

Comparative Example 1

Into a conventional adiabatic, fixed-bed radial type reactor for commercial production of styrene wherein gas stream flows from the core of the cylindrical catalyst bed radially toward outer portion of the cylindrical bed (capacity: about 200,000 ton/year) was inserted a pair of partitions of 10-mesh stainless steel screens placed apart from each other and rectangular to the axis of the cylindrical catalyst bed thereby to define a small room within the reactor, and a $Fe_2O_3$-$K_2O$-$Cr_2O_3$ catalyst containing about 10.6 wt% of $K_2O$ ("S-105" produced by Shell Corp.) was packed in the small room fully from the inlet (core) with respect to the gas flow direction to the outlet. A catalyst to be used for commercial operation was packed in the space within the reactor other than the small room in which S-105 was packed, and dehydrogenation reaction was conducted continuously for about 11 months under commercial running conditions at a molar ratio of steam/ethylbenzene of 12 or less.

Then, the catalyst S-105 packed in the small room was taken out and evaluated. First, little powdering of the used catalyst was observed from the gas inlet portion to the outlet portion. Next, in order to determine the activity of the catalyst S-105 at the time of the end of the use for 11 months', dehydrogenation reaction was conducted over the used catalyst in the reactor used in the model test referred to hereinbefore under the conditions of atmospheric pressure, steam/ethylbenzene molar ratio of 11, LHSV of one Hr$^{-1}$, catalyst amount of 50 ml, and reaction temperature of 600° C.

The results obtained were ethylbenzene conversion of 60% and styrene selectivity of 91%.

Comparative Example 2

Similarly as in Comparative Example 1, small room was provided within a commercial plant reactor by means of a pair of partitions of a 10-mesh stainless steel screens, and a catalyst of $Fe_2O_3$-$K_2O$-$CeO_2$ containing about 22.5% of $K_2O$ ("G-64" produced by Girdler Co.) was packed in the small room fully from the inlet with respect to the gas flow direction to the outlet. Dehydrogenation was conducted on the reactor under entirely the same conditions as in Comparative Example 1, and the catalyst G-64 packed in the small room was taken out for evaluation.

The used catalyst was observed to be entirely powdered and the bed of the catalyst disappeared at the portion corresponding to 20% of the length from the gas inlet portion. Also, near the core portion, concretion of the catalyst particles was found to have occurred and powdered catalyst particles were found.

Example 1

The reactor used in Comparative Example 1 was used except for the use of two types of cataysts so that 15 volume percent of the small room near the core was packed with catalyst S-105 and the remainder (85%) of the small room with catalyst G-64 whereby the gas stream was to flow first through the bed of S-105 and then through the bed of G-64.

Dehydrogenation was conducted on the reactor under entirely the same conditions as in Comparative Example 1, and the two types of catalysts were taken out for evaluation.

Little powdering and no concretion of the catalyst were observed. The used two types of catalysts were admixed, and the mixture was subjected to dehydrogenation under the same conditions as in Comparative Example 1 except that the reaction temperature was set at 620° C.

As a result, ethylbenzene conversion was found to be 63%, and styrene selectivity 95%.

From the above Example 1 and Comparative Examples, it can be clearly seen that the method of the present invention affords higher yield and longer catalyst life under the condition of low steam/starting material alkylbenzene ratio.

Example 2

Dehydrogenation was conducted with the use of the reactor used in and under the conditions used in Comparative Example 1 except for the use in the small room of a uniform mixture of the catalyst S-105 and G-64 at a ratio of 3:7 packed fully from the gas inlet to the gas outlet.

Powdering at the gas inlet portion was found to be less as compared with Comparative Example 2. No concretion phenomenon occurred at all. The catalytic activity of the mixture of the two types of catalysts after the use for dehydrogenation was conducted as in Example 1.

As a result, ethylbenzene conversion was found to be 64%, and styrene selectivity 93%.

From the above Example and Comparative Examples, it can clearly be seen that according to the method of the present invention alkylbenzene can be obtained in high yield, and the catalyst life can be prolonged even under the condition of low steam/starting alkylbenzene ratio.

What is claimed is:

1. In a method for producing an alkenylbenzene by catalytically dehydrogenating an alkylbenzene under a non-oxidative condition in the presence of steam in the reaction zone comprising a fixed-bed of potassium-based dehydrogenation catalyst particles, the improvement in which (a) said fixed-bed comprises particles of at least two kinds of potassium-based dehydrogenation catalyst with respectively different potassium contents and (b) the catalyst particles with higher potassium content are not disposed on the upstream side of said fixed-bed with respect to said reaction.

2. A method according to claim 1, wherein the improvement (b) is achieved by arranging the catalyst particles with higher potassium content on the downstream side of said fixed-bed with respect to said reaction and the catalyst particles with lower potassium content on the upstream side of said fixed-bed with respect to said reaction.

3. A method according to claim 1, wherein the improvement (b) is achieved by mixing substantially homogeneously the catalyst particles with higher potassium content with the catalyst particles with lower potassium content, thereby making the potassium content in said fixed-bed substantially homogeneous from the upstream side to the downstream side of said catalyst bed.

4. A method for preventing a potassium-based dehydrogenation catalyst for catalytical dehydrogenation of alkylbenzene under non-oxidative conditions in the presence of steam from being degraded during the dehydration process, which method comprises (a) using a fixed-bed comprising at least two kinds of potassium-based dehydrogenation catalyst particles of respectively different potassium contents, (b) the catalyst particles with higher potassium content not being arranged on the upstream side of the catalyst bed.

5. A method according to claim 4, wherein the measure (b) is accomplished by arranging the catalyst particles with higher potassium content on the downstream side of said fixed-bed with respect to said reaction and the catalyst particles with lower potassium content on the upstream side of said fixed-bed with respect to said reaction.

6. A method according to claim 4, wherein the measure (b) is accomplished by mixing substantially homogeneously the catalyst particles with higher potassium content with the catalyst particles with lower potassium content, thereby making the potassium content in said fixed-bed substantially homogeneous from the upstream side to the downstream side of said catalyst bed.

* * * * *